United States Patent [19]

Green

[11] Patent Number: 5,158,567

[45] Date of Patent: Oct. 27, 1992

[54] ONE-PIECE SURGICAL STAPLE

[75] Inventor: David T. Green, Westport, Conn.

[73] Assignee: United States Surgical Corporation, Norwalk, Conn.

[21] Appl. No.: 707,999

[22] Filed: May 23, 1991

Related U.S. Application Data

[60] Continuation of Ser. No. 284,410, Dec. 14, 1988, abandoned, which is a division of Ser. No. 92,076, Sep. 2, 1987, Pat. No. 4,821,939.

[51] Int. Cl.⁵ .............................................. A61B 17/00
[52] U.S. Cl. ................... 606/219; 227/902; 411/457; 411/920
[58] Field of Search ........................ 606/219; 227/902; 411/457, 920

[56] References Cited

U.S. PATENT DOCUMENTS 4,399,810  8/1983  Samuels et al. ............... 128/337
4,526,174  7/1985  Froehlich ..................... 128/335
4,719,917  1/1988  Barrows et al. ................ 128/334 R Primary Examiner—Stephen C. Pellegrino
Assistant Examiner—Gary Jackson
Attorney, Agent, or Firm—Thomas R. Bremer

[57] ABSTRACT

The anvilless surgical stapler includes a pair of stapling assemblies which are mounted on the articulated handles of an applicator. Each stapling assembly includes a mounting block and a staple cartridge which is slidably mounted within the block. Further, each cartridge has a housing with a plurality of openings in which staples are slidably received along with a plurality of pushers. When the stapling assemblies are brought together, one or more ribs in the mounting blocks cause the pushers to fire the staples from the openings of the staple cartridge housings. A pair of deformable lips are also provided at the mouth of each opening for deforming the legs of each staple inwardly toward each other in order to embed into the tissue without penetrating into the tissue. The lips also permit passage of the deformed staples under the biasing force of the pushers.

4 Claims, 5 Drawing Sheets

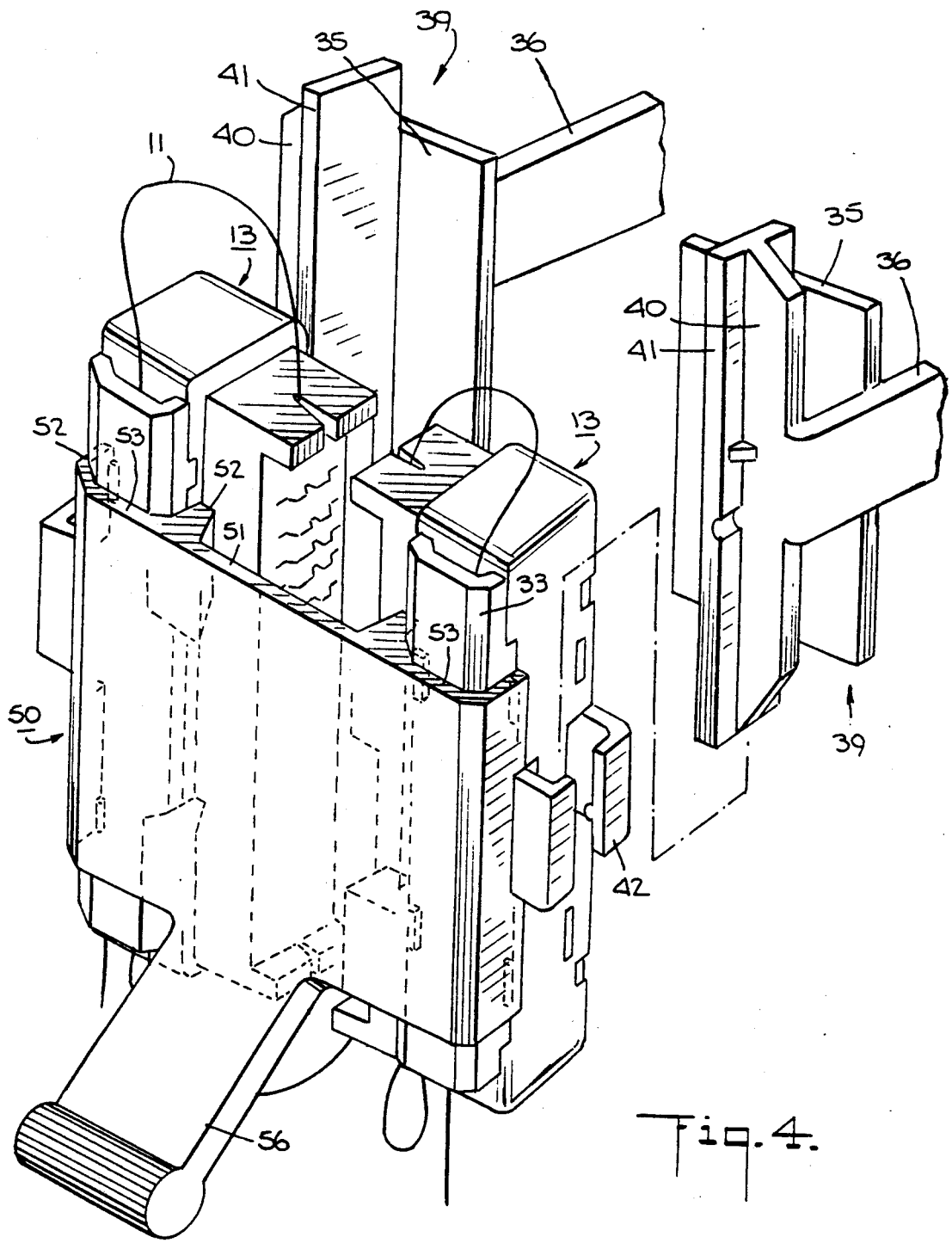

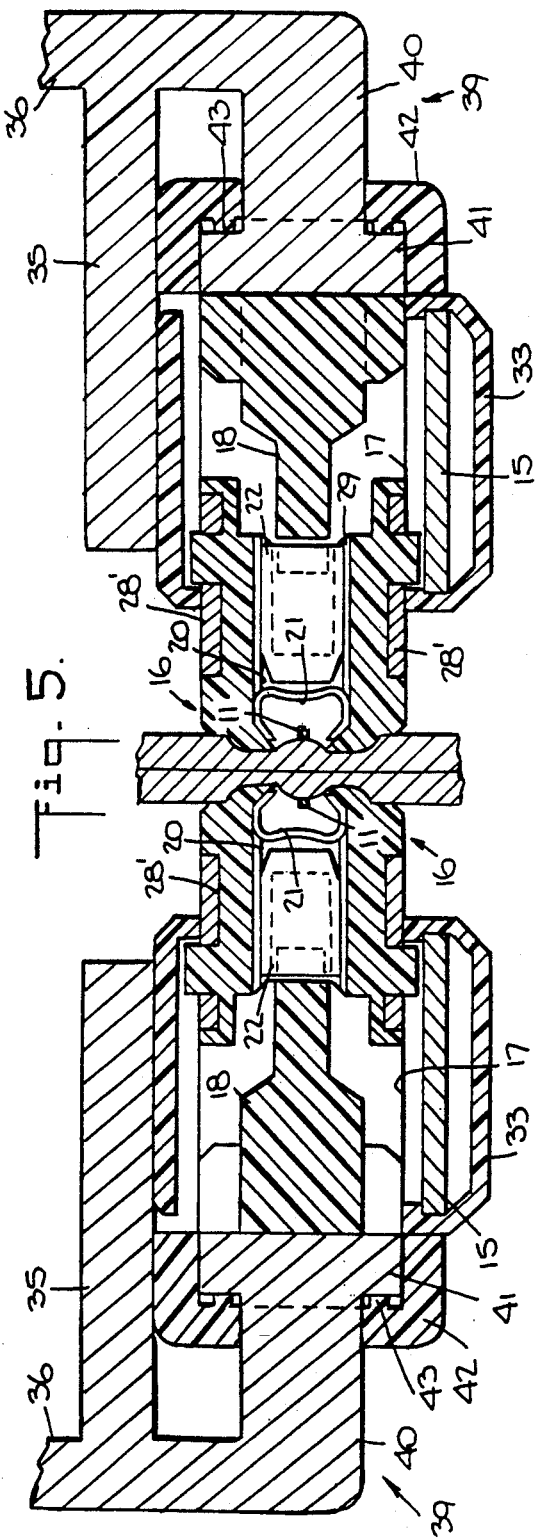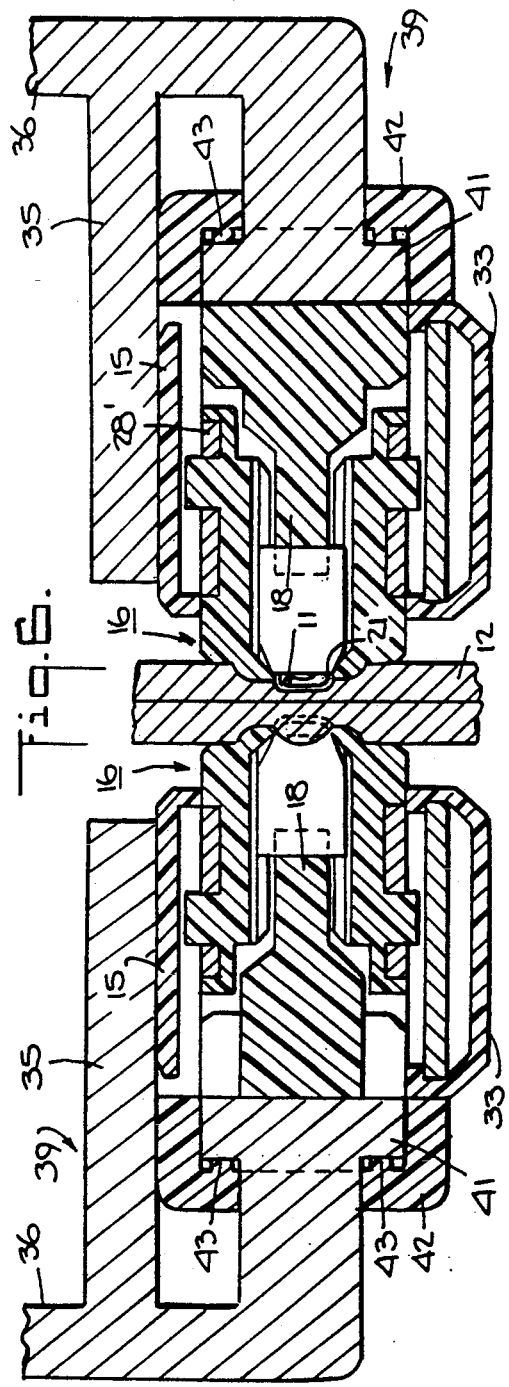

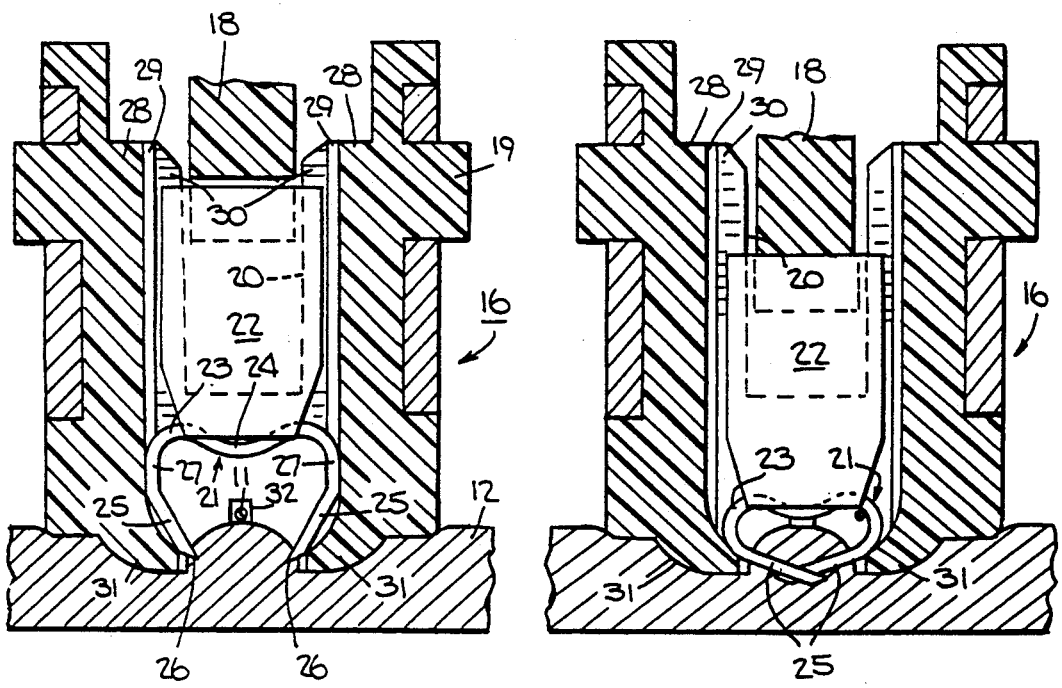

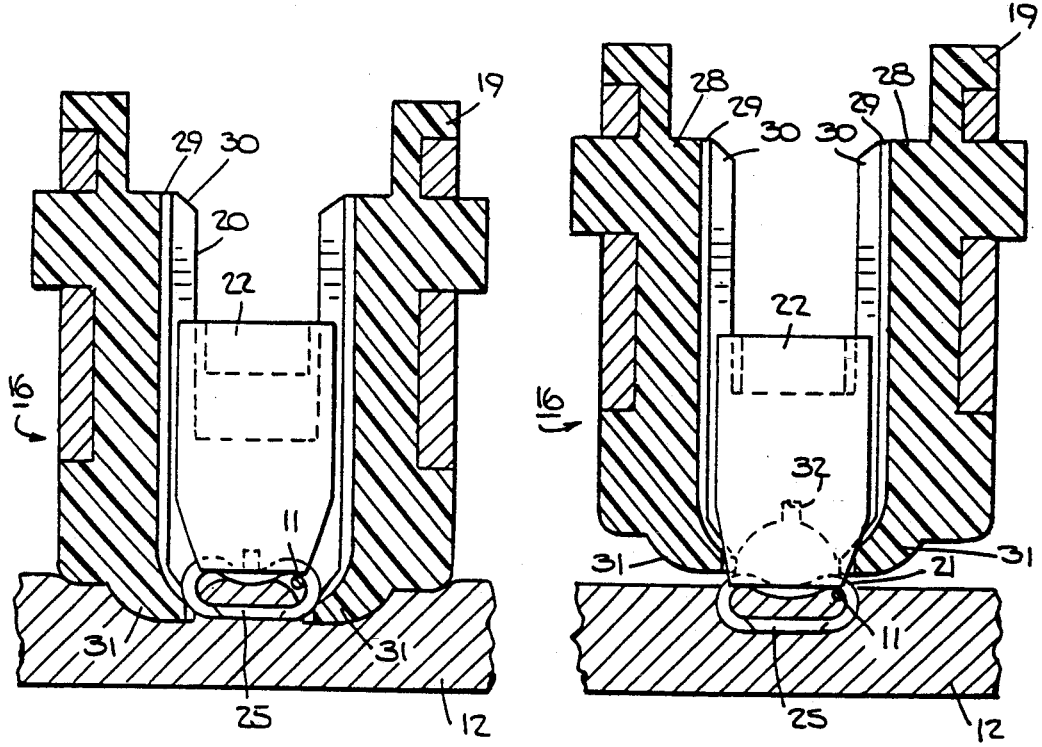

ONE-PIECE SURGICAL STAPLE

This is a continuation of co-pending application Ser. No. 284,410, filed on Dec. 14, 1988, now abandoned, which is a division of Ser. No. 092,076, filed on Sep. 2, 1987, now U.S. Pat. No. 4,821,939.

This invention relates to a staple cartridge and, more particularly, to an anvilless surgical stapler and a method of affixing a staple to tissue.

Heretofore, various types of stapling instruments have been known for affixing staples to body tissue. Generally, the staples have been applied by using instruments having an anvil and an ejector mechanism for driving the legs of a staple through the tissue and against the anvil for deforming the legs into a "B" shape or the like. In some cases, the stapling instruments have been used to apply a purse string to the tissue, for example, for an end to end anastomosis procedure.

Although various types of instruments have been known for driving the legs of a staple through tissue, there are times when it is not desirable or practical to drive the legs of a staple through the body tissue in order to affix a staple. For example, it is generally not practical to use a stapling instrument having an anvil for closing an incision in fascia tissue since there is usually limited space for access of an anvil. Further, in cases where a purse string is to be applied to a tubular section of tissue, the stapling instruments have been rather cumbersome and complex in order to provide an anvil against which the staples can be deformed in order to hold a purse string in place.

Accordingly, it is an object of the invention to affix a staple to body tissue without complete piercing of the tissue by the legs of the staples.

It is another object of the invention to provide a staple which can be affixed to body tissue without complete s piercing of the tissue.

Briefly, the invention provides a one-piece staple which can be affixed to tissue without complete piercing of the tissue. In this regard, the staple has a base of a shape to define one of a recess and a projection and a pair of deformable legs which extend from the base with each leg extending angularly inwardly of the base towards the other leg. In addition, each leg has a sharp point at a distal end for penetrating into body tissue. The staple also includes a pair of rounded transition portions each of which extends between the base and one of the legs.

These and other objects and advantages of the invention will become more apparent from the detailed description taken in conjunction with the accompanying drawings wherein:

FIG. 4 illustrates an enlarged exploded view of a cartridge assembly for mounting on an applicator in accordance with the invention;

FIG. 5 illustrates a cross sectional view of the surgical stapler assemblies in a tissue-clamping position;

FIG. 6 illustrates a cross sectional view similar to FIG. 5 of the stapling assemblies in a fired position in accordance with the invention.

FIG. 7 illustrates a partial view of a stapling assembly in an initial deformation position;

FIG. 8 illustrates a view similar to FIG. 7 during further deformation of a staple in accordance with the invention;

FIG. 9 illustrates a view similar to FIGS. 7 and 8 of a deformed staple in accordance with the invention;

FIG. 10 illustrates a view similar to FIGS. 7, 8 and 9 with a deformed staple expelled from a stapling assembly in accordance with the invention;

Figure 1:
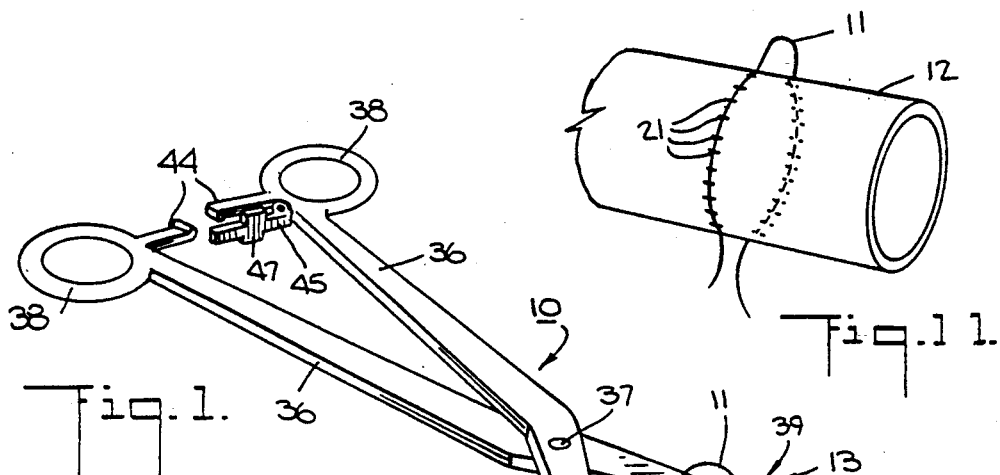
FIG. 1 illustrates a perspective view of an anvilless surgical stapler for applying a staple constructed in accordance with the invention.

Referring to FIG. 1, the anvilless surgical stapler is used, for example for applying a purse string 11 to a tubular section of tissue 12. In this respect, the term "anvilless" means that there is no opposing anvil or separate member to deform the legs of a staple. As indicated, the stapler 10 includes a pair of stapling assemblies 13 and an applicator 114 constructed in the manner of a forceps.

Referring to FIG. 7, each stapling assembly 13 includes a mounting block 15 and a staple cartridge 16 slidably mounted in the mounting block 15. Each of the mounting block 15 and staple cartridge 16 is of elongated rectangular shape.

Referring to FIG. 5, the mounting block 15 includes an internal recess 117 for slidably receiving a staple cartridge 16 as well as a centrally disposed rib 118 Within the recess 17. This rib 18 is fixedly secured to the remainder of the block 15. This rib 18 may extend longitudinally of the block 15 or a plurality of discrete ribs 1(not shown) may be used.

Referring to FIG. 7, each staple cartridge 16 includes a housing 19 having a plurality of longitudinally spaced apart openings 20 in each of which a staple 21 is slidably received. In addition, a plurality of pushers 22 are slidably mounted within the housing 19 with each pusher 22 being aligned with an opening 20 and a staple 21 therein as well as in alignment with a rib 18 for abutting there against.

Referring to FIG. 7, each staple 21 is of one-piece construction having a base 23 of undulating shape to define a recess 24 and a pair of deformable legs 25 which extend from the base 23. As indicated, each leg 25 extends angularly inwardly of the base 23 towards the other leg 25 and has a sharp point 26 at the distal end.

Each staple 21 also includes a pair of rounded transition portions 27 each of which extends between the base 23 and a leg 25. Further, each leg 25 is disposed on a rectilinear axis with the sharp point defined, for example by an included angle of 35°. The staple 21 is made of any suitable cross section, such as a circular cross-section as well as of any suitable material for the purposes intended such as stainless steel and absorbable materials.

Referring to FIG. 7, the housing 119 has a pair of opposed walls 28 defining each internal opening 20. In addition, each wall 28 is provided on the outside with a stiffener plate 28' and has a first slot 29 extending longitudinally of the opening 20 in order to slidingly receive one side of a staple 21, that is, a rounded transition portion 27. In addition, a second slot 30 of greater width than the slot 29 extends coaxially of the slot 29 in order to slidably receive one side of a pusher 22.

As indicated in FIG. 7, the width of a staple 21 is greater than the width of a pusher 22. Further, the lower surface of each pusher 22 is provided with a surface complementary to the undulating base 23 of a staple 21 so as to have a projection (not shown) seated in the recess 24 of the staple 21. This arrangement serves to center the staple 21 within the opening 20 while also ensuring uniform motion of a staple 21 out of the opening 20.

A means for deforming the legs 25 of a staple 21 at the mouth of each opening 20 is constituted by a pair of inwardly directed lips 31. As indicated, each lip 31 is disposed at one end of the staple receiving slot 29 in a wall 28 Further, the lips 31 are spaced apart to define an outlet of less width than the opening 20 and less width than a staple 21. In this respect, the housing 19 is made of a material sufficient to permit deformation of the legs 25 of a staple 21 while at the same time being deformable to spread apart to permit passage of a deformed staple 21 under a biasing force on the respective pushers 11. Each lip 31 may also be of material resilient enough to permit the passage of a deformed staple while still capable of returning to its previous position and form. Such resiliency is required if successive staples are fired as, for example, in a skin stapler. Additionally, lips 31 may have an articulation means for achieving such resiliency.

As indicated in FIG. 7, the tip of each staple leg 25 1 is angled such that the heel (i.e. rear) of the angled tip slides within a slot 29 so that the sharp tip does not dig into the lip 31 during firing. In this respect, the slot 29 is curved within the lip 31.

Referring to FIGS. 5 and 6, the ribs 18 constitute a means for moving the pushers 22 from a rest position in the respective housings 19, as indicated in FIG. 5, to an actuated position, as indicated in FIG. 6, adjacent the outlet of each opening 20. In this respect, a suitable means such as a bar may be connected to one or more pushers 22 in order to move the pushers simultaneously.

Figure 11:
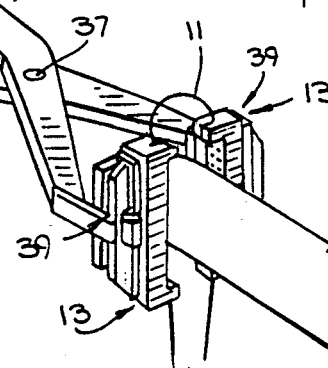
FIG. 11 illustrates a tubular section of tissue having a purse string applied thereto by the staple of FIG. 1.

As indicated in FIGS. 7 and 11, each housing 19 includes a recess 32 which extends along the housing 19 transversely of and across the respective openings 20 to receive a purse string 11.

The openings 20 and respective staples 21 of each cartridge 16 are offset longitudinally of the openings 20 and staples 21 of the opposed cartridge 16. This allows the clamped tissue 12 to protrude into the openings 20 and also inhibits the staples 21 from penetrating both sides of the tissue 12.

Referring to FIG. 4, each stapling assembly 13 includes a retainer 33 which is mounted in fixed relation on a mounting block 15. As indicated, each retainer 33 defines an elongated space within which a loop of the string 11 may be retained.

As also indicated in FIG. 4, each cartridge 16 has a projection extending from each end of the housing 19 for abutting an opposed cartridge 16 in order to define a tissue-receiving gap between the cartridges 16. This gap is such as to avoid crushing of the tissue. Further, each projection 34 can be provided with a recess 35 to receive a length of the purse string 11 therein.

The projections 34 also serve to transfer the forces necessary to fire the stapler. Alternatively, each staple cartridge may have a single projection at each end which is about half the width of a cartridge housing 19 so as to abut an aligned cartridge housing 19 while aligning with a similar projection of the opposed cartridge. In this case, the purse string would extend between the two projections at each end of the cartridges.

Referring to FIG. 1, the applicator 14 includes a pair of mounting plates 35 which are disposed in opposed relation to each other and a pair of articulated handles 36 which are connected to the mounting plates 35 for moving the plates 35 towards each other. As indicated, the handles 36 are pivotally connected to each other about a pivot pin 37. Also, each handle 36 includes a finger gripping portion 38 at a proximal end. A spring (not shown) may also be provided to bias the handles 36 apart.

Referring to FIG. 4, each mounting plate 35 has means 39 for mounting a respective stapling assembly 13 thereon. As indicated, each means 39 includes a bracket 40 integral with a plate 35 from which a mounting leg 41 extends in spaced relation to the mounting plate 35. In addition, each stapling assembly 13 is provided with a sleeve-like connector 42 which releasably receives a mounting leg 41. A suitable detent (not shown) may be provided in the sleeve connector 42 to be releasably engaged in a groove 43 of the mounting leg 41.

In order to mount a stapling assembly 13 in place, the sleeve connector 42 is slid over a mounting leg 43 until the detent (not shown) catches in the groove 43 of the mounting leg 41.

Figure 2:
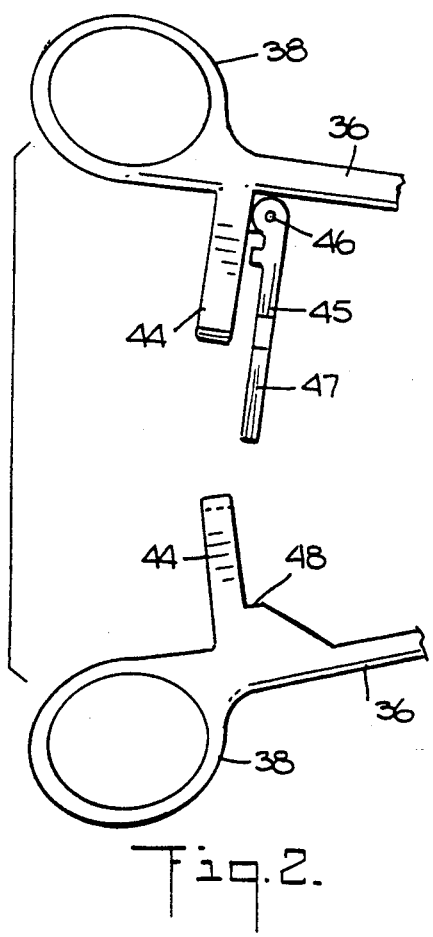
FIG. 2 illustrates a partial view of a safety mechanism employed with the handles of the stapler of FIG. 1.
Figure 12:
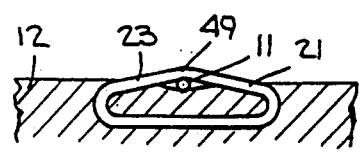
FIG. 12 illustrates a modified staple constructed in accordance with the invention.
Figure 3:
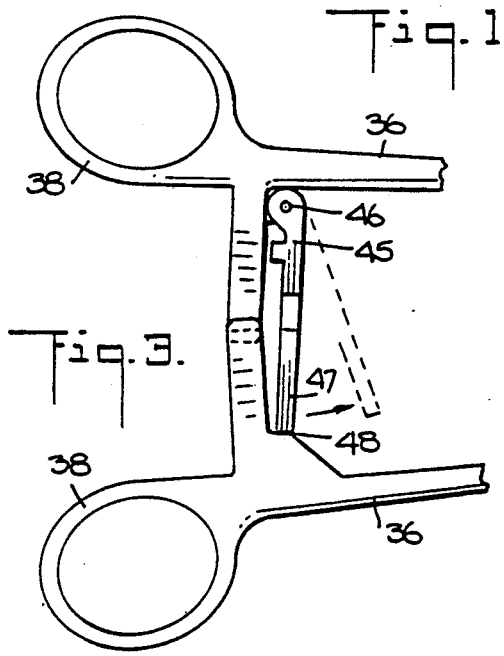
FIG. 3 illustrates a view of the safety mechanism in a tissue-clamping position.

Referring to FIG. 11, the applicator 10 includes a catch mechanism 44 which serves to approximate a predetermined clamping position of the applicator 10. This mechanism 44 is disposed on the handles 36 at the proximal ends and is of generally known construction and need not be further described. In addition, a safety mechanism 45 is provided at the proximal end for stopping the handles 36 in a tissue-clamping position (as indicated in FIG. 6) with the projections 34 abutting a respective cartridge 16. As indicated in FIGS. 11 and 2, the safety mechanism 45 is in the form of a lever which is pivotally mounted about a pin 46 on the catch mechanism 44 and includes a lateral tab 47 which is sized to permit pivoting of the lever 45 by a thumb of a surgeon. As indicated in FIG. 3, when in the tissue-clamping position, the lever 45 abuts against an abutment surface 48 on the opposite handle 36 while the catch mechanism 44 holds the handles 36 in place.

Referring to FIG. 4, a holder 50 is provided to releasably hold a pair of stapling assemblies 13 in order to form a cartridge assembly. As indicated, the holder 50 is formed of a base plate 51 with a plurality of ribs 52 on one side forming a pair of parallel spaced apart grooves 53 for receiving a retainer of each stapling assembly 13. In addition, means are provided for releasably engaging each retainer 33 in a respective groove 33. For example, the means may be in the form of small projections 54 which fit into small spaces 55 between each retainer 33 and a mounting block 15 of a stapling assembly 13 (see FIG. 5). As indicated, the grooves 53 may be dis-continuous, that is the internal ribs 52 need not extend the length of the plate 51. Alternatively, the holder 50 may grip the assemblies 13 at the ends rather than the sides as shown.

The holder 50 is also provided with an outwardly extending tab 56 at one end of the plate 51. This tab 56 serves to lift the plate 51 from the stapling assemblies 13 after mounting of the assemblies 13 on the mounting plates 35 on the handles 36 of the applicator 14. Alternatively, instead of using a tab 56, a pair of finger engaging recesses may be provided on opposite ends of the plate 51, for example on the lower end of the plate 51 as viewed in FIG. 4.

In use, the stapler 10 may be provided with the stapling assemblies 13 in place. If not, a cartridge assembly as indicated in FIG. 4 may be brought to the mounting plates 35 with the handles 36 in an opened rest position. At this time, the stapling assemblies 13 can be slid onto the respective mounting legs 41 and snap-fitted in place. Thereafter, the holder 50 can be removed, for example, by a slight tilting up of the plate 51 from the retainers 33.

Thereafter, the stapler 10 can be brought into position about a tubular section of tissue 12 as indicated in FIG. 1 Next, the handles 36 can be brought into a tissue-clamping position with the catch mechanism 44 engaged and the safety mechanism lever 45 in abutment with the surface 48 as indicated in FIG. 3. At this time, the projections 34 of the staple cartridges 16 are in abutment with the tissue 12 in a collapsed condition as indicated in FIG. 7. At this point, the staples 21 have not been engaged by the pushers 22. Further, the stapler 10 can be opened and re-positioned by moving the handles 36 apart in this position without projection of the staplers 21 from the cartridges 16.

Next, the safety mechanism 45 is released into the dotted line position of FIG. 3 and the handles 36 are brought further together in order to fire the staples 211 from the cartridges 16 as indicated in FIG. 6.

As indicated in FIGS. 7 to 10, during firing, each staple 21 is deformed into a layer of tissue 12 without piercing through the tissue layer. Initially, as indicated in FIG. 7, the deformable legs 25 of the staple abut against the deformable lips 311 with the sharp ends 26 projecting into the mouth of a respective opening 20. The layer of tissue 12 deforms about the lips 31 so as to enter slightly into the mouth of each opening 20 and may be slightly penetrated by the sharp tips of the staples 21.

As the handles 36 are brought together, the mounting blocks 15 of the staple assemblies 13 move toward each other as indicated in FIG. 6. However, the housings 19 of the respective staple cartridges 16 remain in place. That is, each mounting block 15 moves relative to the stapled cartridge 16 therein. At this time, the rib 18 of each mounting block 15 abuts the pushers 22, or a bar common to the pushers 22, so as to drive the pushers 22 towards the mouth of each opening 20 as indicated in FIG. 8.

Initially, as indicated in FIG. 10, each staple 21 is pushed under a biasing force applied to the base 23 while lateral forces are simultaneously applied against the legs 25 by the lips 31 so that the legs 25 begin to deform and move towards each other while penetrating into the layer of tissue 21.

As indicated in FIG. 9, near the end of each stroke of a pusher 22, the legs 25 of a staple have been substantially deformed so as to be in parallel crossing relation to each other. In this position, the staples will not readily pull out from the layer of tissue 12. At the same time, the string 11 which has been positioned in the longitudinal recess 32 of a cartridge housing 19 is pushed out of the recess 32 to one or the other side of the deformed staple 21.

As indicated in FIG. 9, the deformed staple 21 is of greater width than the mouth of the opening 20 so as to engage against the deformable lips 31.

Referring to FIG. 10, as the stroke of a pusher 22 is completed, the biasing force on the pusher 22 is sufficient to push the deformed staple 21 through the outlet of the mouth of the opening 20 past the lips 31 while deforming the lips 31 sufficiently to permit passage. The amount of deformation of the lips 31 is sufficient to permit passage of the deformed staple 21 while at the same time being insufficient to overly compress the layer of tissue 12.

Once the stapler has been fired, the purse string 11 is automatically pulled from the retainers 33 as the stapler 10 is removed from the area.

Of note, the staples 21 only penetrate the tissue 12 to a depth sufficient to remain embedded as the string 11 is drawn and the tissue 12 bunched together in a subsequent operation. In this respect, a purse string normally ties the end of an opening in the hollow tissue such as an intestine, stomach and the like.

After firing of the staples 21, the handles 36 can be held in place by the catch mechanism 44. Alternatively, the catch mechanism 44 can be released so that the handles 36 are biased apart by the spring (not shown) therebetween.

As indicated in FIG. 11, after removal of the stapler 10, the purse string 11 is held in place by the various staples which have been affixed to the tissue 112. Of note, depending upon the shifting of the string 11 to one side or the other within a staple 21, the string 11 may take a somewhat uneven path about the tissue 12.

Referring to FIG. 14, in order to centralize the string 11, the base 23 of each staple 21 may be provided with a projection for reception in a suitable mating recess in the bottom surface of a pusher (not shown). In this case, as each staple is being expelled, the purse string 11 tends to be centered within each deformed staple 21'.

Various modifications may be made within the stapler. For example, the mounting arrangement of a staple cartridge on the applicator may be modified. For example, the mounting block of each cartridge may have a pair of tabs which can be slidably received in a mounting head on the end of a handle 36.

Further, each staple may be made with a flat base and/or with legs that are angled toward each other and are sized so as not to cross each other when deformed depending on the use of the staple, for example, for closing an incision rather than for application of a purse string.

The invention thus provides a stapler which can be utilized for applying a purse string to body tissue. However, the stapler may also be used as a skin or fascia stapler in which case use may be made of only one staple assembly. Where only one staple assembly is used, the staples may be fed and deformed singly. Also, the stapler may be constructed and adapted for use in eye surgery for the closing of incisions.

The invention also provides a method of affixing a staple to tissue wherein a biasing force is applied to the base of a staple to push the legs of the staple into the tissue while simultaneously applying lateral forces against the legs to deform each leg toward the other leg. Such forces are applied to the staple without any opposed force as from an opposed anvil.

What is claimed is:

1. A one-piece staple comprising
a base of undulating shape defining a recess on one side and a projection on an opposite side;
a pair of rounded transition portions extending from opposite ends of said base; and
a pair of deformable legs, each said leg extending from a respective transition portion on a rectilinear axis towards the opposite leg with a sharp point at a distal end and being deformable inwardly towards said base to be in parallel crossing relation with said other leg while said undulating shape of said base is retained.

2. A one-piece staple as set forth in claim 1 made of stainless steel.

3. A one-piece staple as set forth in claim 1 wherein said sharp point is defined by an included angle of 35°.

4. A one-piece staple as set forth in claim 1 wherein said base and said legs gave a circular cross-section.

* * * * *